United States Patent [19]
Wagner

[11] 3,947,689
[45] Mar. 30, 1976

[54] AUTOMATIC SYSTEM FOR PRECISE COLLIMATION OF RADIATION

[75] Inventor: Howard G. Wagner, New Canaan, Conn.

[73] Assignee: The Machlett Laboratories, Inc., Stamford, Conn.

[22] Filed: May 6, 1974

[21] Appl. No.: 467,411

Related U.S. Application Data

[62] Division of Ser. No. 354,826, April 26, 1973, Pat. No. 3,863,073.

[52] U.S. Cl. ............................... 250/512; 250/511
[51] Int. Cl.² ........................................... G21F 5/04
[58] Field of Search ................... 250/445, 511, 512

[56] References Cited
UNITED STATES PATENTS

| | | | |
|---|---|---|---|
| 2,921,202 | 1/1960 | Berger et al. | 250/511 |
| 3,130,313 | 4/1964 | Tilling | 250/511 |
| 3,502,872 | 3/1970 | Norgren | 250/511 |
| 3,502,878 | 3/1970 | Stewart et al. | 250/512 |
| 3,511,995 | 5/1970 | Lombardo | 250/511 |
| 3,581,094 | 5/1971 | Peyser et al. | 250/320 |
| 3,643,095 | 2/1972 | Shuster | 250/445 |

Primary Examiner—Archie R. Borchelt
Assistant Examiner—B. C. Anderson
Attorney, Agent, or Firm—John T. Meaney; Joseph D. Pannone; Harold A. Murphy

[57] ABSTRACT

A radiographic system comprising a radiation source disposed to direct a beam of radiation through an adjustable aperture in an aligned beam-limiting device and onto an image receptor located at a selected distance from the source, and automatic means for making a unidirectional final adjustment of the aperture to provide the beam with a cross-sectional area which conforms to the size of the image receptor at the selected distance from the source.

17 Claims, 10 Drawing Figures

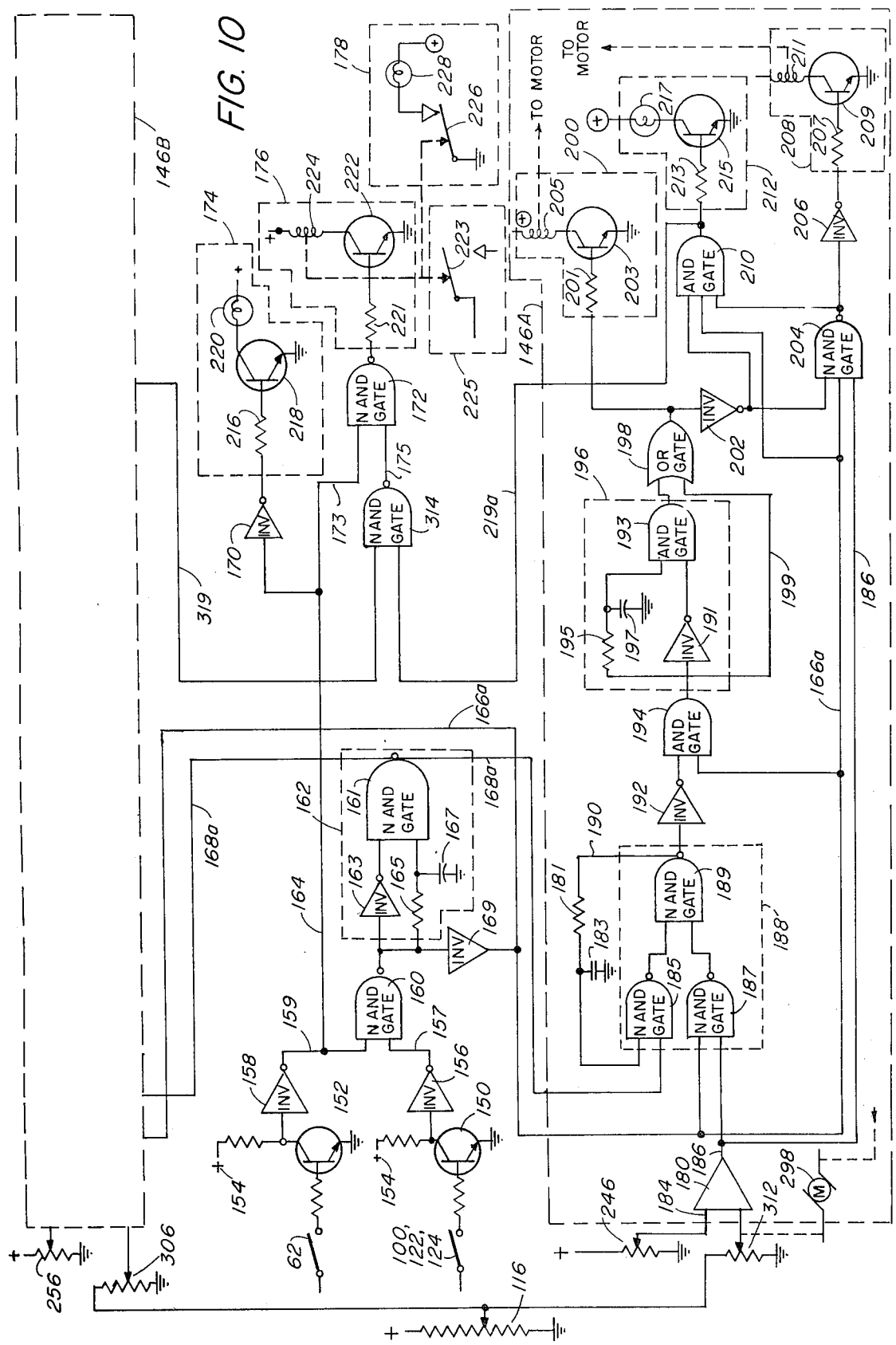

AUTOMATIC SYSTEM FOR PRECISE COLLIMATION OF RADIATION

CROSS-REFERENCE TO RELATED APPLICATIONS

This is a division of application Ser. No. 354,826, filed Apr. 26, 1973, now U.S. Pat. No. 3,863,073.

BACKGROUND OF THE INVENTION

This invention relates generally to automatic collimating systems and is concerned more particularly with a radiographic system having adjustable beam collimating means for protecting a person from overexposure to radiation.

It is well-known that internal organs of a human body, for example, may be examined by exposing a preselected region of the body to radiation, such as X-rays, for example, for a limited period of time. However, the radiation should be confined to the specific area of the body under examination in order to minimize exposure of the patient to the radiation. This objective is best achieved by precisely regulating the cross-sectional size of the beam irradiating the area of the body being examined.

One type of X-ray apparatus particularly suitable for achieving this objective is shown and described in U.S. Pat. No. 3,581,094 granted to L. F. Peyser et al and assigned to the assignee of this invention. The apparatus disclosed therein includes a beam limiting device or collimator having two orthogonally arranged pairs of opposing pivotal plates which form a rectangular aperture. The plates are made of X-ray absorbent material, such as lead, for example, and serve to regulate the cross-sectional size and shape of a beam passing through the aperture. In accordance with electrical signals produced by sensing devices suitably located in the apparatus, the rectangular aperture is adjusted to provide the beam with a cross-sectional size conforming substantially to the rectangular area of an X-ray film. Thus, when a patient is positioned between the beam limiting device and the X-ray film, only the portion of the patient's body selected for study should be irradiated and imaged on the film.

Another type of beam limiting device, which is more suitable for regulating the diametric size of an X-ray cone is shown and described in U.S. Pat. No. 3,448,270 granted to L. F. Peyser and assigned to the assignee of this invention. Briefly, this patent discloses a beam limiting device having an exit aperture defined by a thimble-like shutter comprising a plurality of X-ray absorbent leaves arranged longitudinally in partial overlapping relationship to form a frusto-conical structure. The leaves are pivotally mounted and simultaneously adjustable to move into greater or lesser overlapping relationship thereby defining the diametric size of a variable aperture at the small diameter end of the frusto-conical structure. Thus, this beam-limiting device may be adjusted to provide a cone of radiation passing through the structure with the proper diameter for impinging on a circular image receptor, such as the input screen assembly of an image intensifier tube, for example.

The described beam-limiting devices generally include means for adjusting the shutter aperture whereby an emerging X-ray beam is provided with a cross-sectional size which conforms substantially to the area of an image receptor. However, recent medical investigations completed by the United States Public Health Service indicate that the cross-sectional size of the X-ray beam, at the plane of the image receptor, should conform even more closely to the surface area of the image receptor than current practice permits. Thus, it has been found desirable to provide automatic means for setting the shutter aperture of the beam-limiting device in a manner which will comply with the recommendations of the United States Public Health Service. Automatic systems for precisely setting the shutter aperture by means of accurate mechanisms which overcome backlash and other forms of hysteresis have proved unsatisfactory, because of the undesirable cost involved and a tendency of the shutters to "hunt" when reaching a desired setting for the aperture. Attempts have been made to overcome this tendency to "hunt" by providing a "dead band" which renders the system insensitive to small amounts of "overshoot" when the shutters reach the desired setting. However, when the aperture is being adjusted, and the shutters reach the desired setting, this small amount of overshoot may result in the X-ray beam having a cross-sectional area which exceeds the allowed tolerances for conforming to the surface area of the image receptor.

Thus, it is advantageous and desirable to provide a radiographic system with a beam-limiting device and means for adjusting the shutter aperture of the device in a manner which overcomes backlash and other forms of mechanical and electronic hysteresis without resorting to prohibitively expensive mechanisms and electronic controls for achieving the desired accuracy.

SUMMARY OF THE INVENTION

Accordingly, this invention provides a radiation source disposed to direct a beam of radiation through an adjustable beam-limiting device and onto an image receptor located at a selected distance from the source, and automatic means for adjusting the aperture to limit the beam to a cross-sectional size which conforms accurately to the size of the image receptor, at the plane of the receptor.

The automatic means includes detecting means for producing electrical signals indicative of the installation of an image receptor in the holder and the selection of a desired source-to-image receptor distance (SID). The automatic means also includes sensing means for producing electrical signals indicative of the image receptor size and the radiation field size at the plane of the image receptor.

The automatic means also includes a collimator monitoring unit including a detector monitoring circuit and a sensor monitoring circuit. The detector monitoring circuit is provided with input means for receiving electrical signals from the detecting means, gating means for producing an electrical signal indicative of an installed image receptor and a selected SID, and one-shot multivibrating means for producing a predetermined time pulse signal in response to a signal from the detector gating means.

The sensor monitoring circuit includes comparator means for receiving electrical signals from the sensing means and producing an output signal indicative of any adjustment required in the aperture size, latched gating means for allowing further manual closing of the aperture but preventing opening of the aperture to a size that allows the radiation field to exceed the receptor except in response to output signals from the detector monitoring circuit and an opening signal from the comparator means, overshoot means for opening the shutter aperture beyond any corrective adjustment required by the comparator means and thereby causing closing of the aperture for a unidirectional final adjustment thereof, and gating means for determining whether the aperture is to close, open or whether corrective adjustment is completed.

In one preferred embodiment, an X-ray source is disposed to direct a generally conical X-ray beam through a substantially circular aperture formed by a frusto-conical shutter in a beam-limiting device and onto a circular input screen assembly of an image intensifier tube located in a suitable holder at a selected distance from the source. Detecting means are provided for producing electrical signals indicative of the location of an image intensifier tube in the holder and the selection of an SID. Sensing means are provided for producing electrical signals indicative of the diametric size of the useful portion of the input screen, the distance of the input screen assembly from the source and the diametric size of the aperture to limit the diametric size of the conical X-ray beam such that it conforms to the circular area of the useful portion of the input screen.

In another preferred embodiment, an X-ray source is disposed to direct a generally conical X-ray beam through a substantially rectangular aperture formed by two orthogonally disposed pairs of opposing plates in a beam-limiting device and onto a rectangular X-ray film clamped in a suitable holder at a selected distance from the source. Detecting means are provided for producing electrical signals indicative of the installation of a film bearing cassette in the holder and the selection of an SID. Sensing means are provided for producing electrical signals indicative of the length and width of the film, the distance of the film from the source and the length and width of the aperture. The collimator monitoring unit is provided with a common detector monitoring circuit feeding output signals into dual sensor monitoring circuits, one for adjusting the length dimension of the shutter aperture and one for adjusting the width dimension thereof. Thus, this collimator monitoring unit provides means for limiting the cross-sectional size of the X-ray beam such that it conforms to the area of an X-ray film to within the desired accuracy.

BRIEF DESCRIPTION OF THE DRAWINGS

For a better understanding of this invention, the following more detailed description makes reference to the accompanying drawings, wherein:

FIG. 10 is a schematic diagrammatic view of a typical embodiment of the invention shown in FIG. 9.

DESCRIPTION OF THE PREFERRED EMBODIMENT

Figure 1:
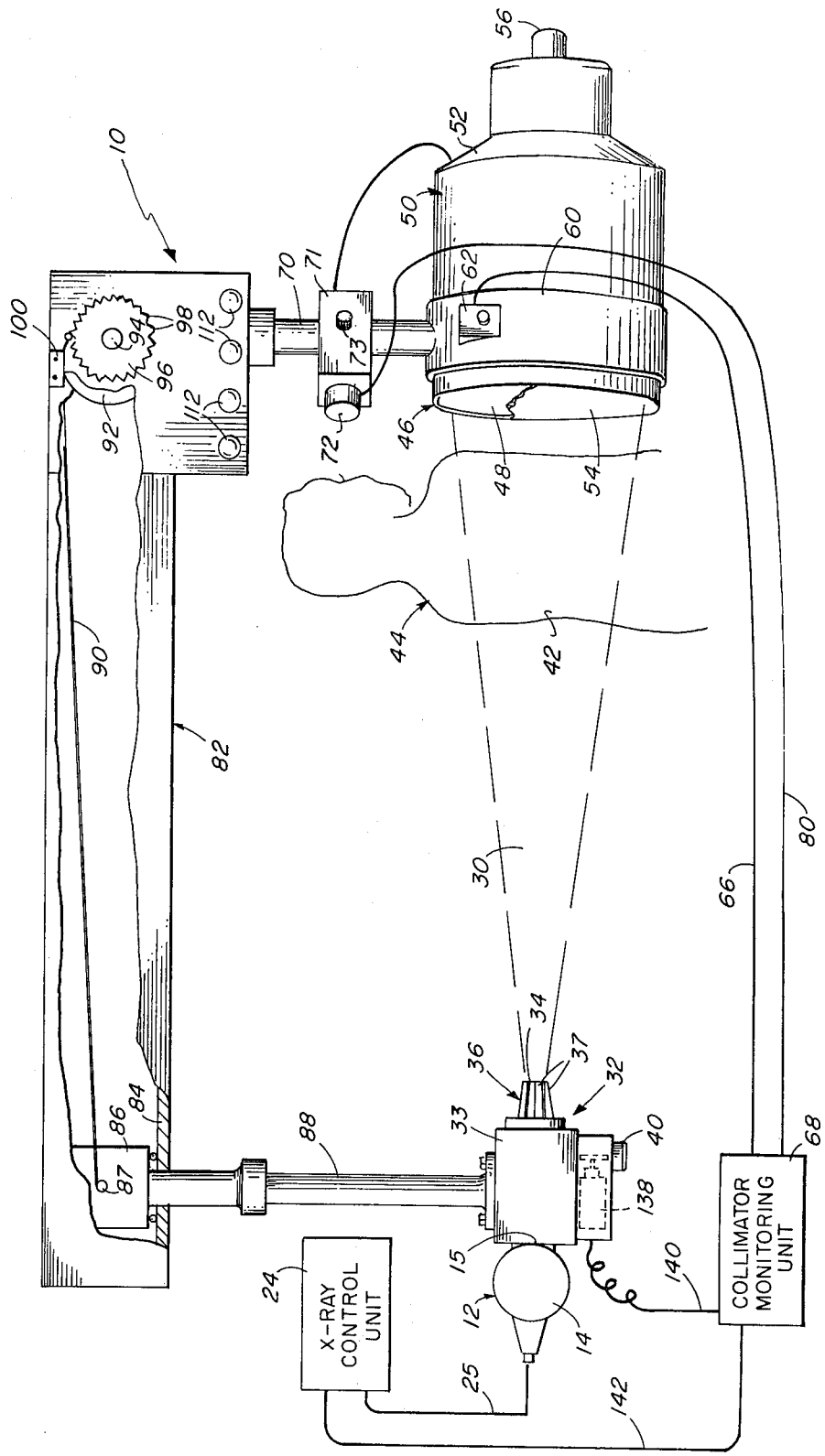
FIG. 1 is a perspective view of one type of radiographic system embodying the invention.
Figure 2:
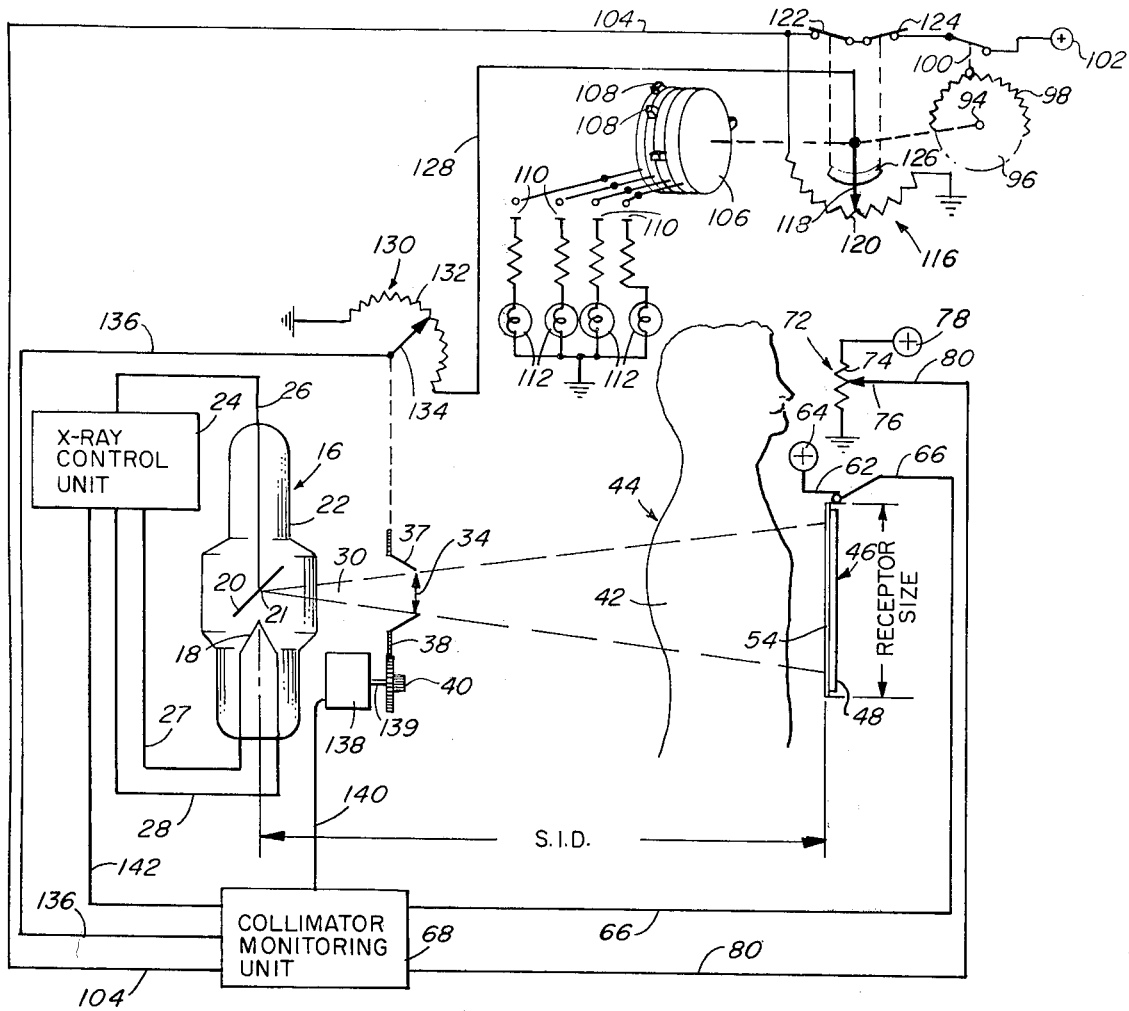
FIG. 2 is a schematic view of the radiographic system shown in FIG. 1.

Referring more particularly to the drawings wherein like characters of reference designate like parts throughout the several views, there is shown in FIGS. 1 and 2 a radiographic system 10 comprising an X-ray generator 12 which includes a hollow cylindrical housing 14 having an X-ray tube 16 longitudinally disposed therein. The X-ray tube 16 may be of any conventional type embodying an electron emitting cathode 18 and a spaced opposing anode 20 within the usual evacuated envelope 22. The electrodes of X-ray tube 16 are electrically connected to an X-ray control unit 24 by suitable means, such as an interconnecting cable 25 having therein an insulated conductor 26 which is connected to the anode 20 and two insulated conductors 27 and 28 which are connected to respective terminal ends of the cathode 18.

In operation, the X-ray control unit 24 supplies electrical current through the conductors 27 and 28 to heat the cathode 18 to a desired electron emitting temperature. By means of conductor 26 and one of the conductors 27 and 28, the X-ray control unit 24 applies suitable electrical potentials to the anode 20 and the cathode 18, respectively, for the purpose of establishing a strong electrostatic field therebetween. The electrostatic field accelerates emitted electrons from the cathode 18 and, in a well-known manner, focusses them onto the anode 20 in a relatively small focal spot area 21 which functions as a point source for a resulting cone 30 of X-radiation emanating therefrom. Thus, it may be seen that the X-ray control unit 24 may prevent the generation of X-ray cone 30 by withholding the electrical potentials applied to the cathode 18 and the anode 20 of X-ray tube 16 by any suitable means.

The cone 30 of X-radiation generated in tube 16 passes through an aligned port 15 in the cylindrical wall of housing 14 and enters a beam limiting device 32 or collimator which may be mounted over the port 15 by any suitable means. The beam limiting device 32 may comprise a housing 33 having an entrance aperture (not shown) adjacent the port 15 of the X-ray generator 12 and an opposing exit aperture 34 defined by a thimble-like shutter 36 which protrudes outwardly of the housing. The shutter 36 is more fully described in the aforementioned U.S. Pat. No. 3,448,270 granted to L. F. Peyser and assigned to the assignee of this invention. Briefly, the thimble-like shutter 36 comprises a plurality of longitudinally extending leaves 37 made of X-ray absorbent material, such as lead, for example, arranged in partial overlapping relationship to form a hollow frusto-conical structure. The leaves 37 are pivotally mounted at the ends adjacent the large diameter opening of the frusto-conical structure and are operatively connected to a rotatable ring 38. Rotation of the ring 38 moves the leaves into greater or lesser overlapping relationship thereby varying the diameter of the exit aperture 34 at the small diameter end of the frusto-conical structure. Thus, the thimble-like shutter 36 limits the diametric size of the X-ray cone 30 as it passes through the beam-limiting device 32.

Located on the exterior of housing 33 is a knob 40 which may be manually adjusted to rotate the ring 38 and thereby vary the diameter of exit aperture 34 in a controllable manner. Thus, the knob 40 provides means for regulating the cross-sectional size of X-ray cone 30 when system 10 is operated in the manual mode. The X-ray cone 30 emerging from the beam limiting device 32 may pass through an aligned portion 42 of a patient 44 and be modified in accordance with a density pattern formed by the internal organs of portion 42, in a well-known manner. Consequently, the modified X-ray cone 30 will convey an X-ray image of these internal organs to an aligned image receptor 46 which may comprise an input screen assembly 48 of an image intensifier tube 50, for example.

A suitable image intensifier tube 50 is shown and described in U.S. Pat. No. 3,417,242 granted to R. W. Windebank and assigned to the assignee of this invention. Briefly, the image intensifier tube disclosed therein comprises a generally cylindrical envelope 52 closed at one end by an input faceplate 54 of preselected diametric size, and at the other end by an output faceplate 56 which is considerably smaller in diameter. Disposed adjacent input faceplate 54 is input screen assembly 48 which converts the incident X-ray image to an equivalent electron image, in a well-known manner. The electron image is electrostatically accelerated from the input screen assembly 48 and focussed onto an output screen assembly (not shown) which is disposed adjacent the output faceplate 56. The output screen assembly converts the accelerated electron image, in a well-known manner, into a bright visible image which is viewable through the output faceplate 56. Thus, the internal organs of portion 42 may be observed while being subjected to X-radiation.

The image intensifier tube 50 may be provided with zooming means comprising a coaxially aligned series of spaced electrodes (not shown) disposed between the input screen assembly 48 and the output screen assembly, as disclosed in the aforementioned Windebank patent. These intermediate electrodes are maintained at respective variable electrical potentials supplied by a remote control unit 71 having a plurality of potentiometers (not shown) therein which may be adjusted by a single control knob 73. The potentials applied to the intermediate electrodes shape the electrostatic field between the input screen assembly 48 and the output screen assembly such that only a portion of the input screen fills the entire output screen. Consequently, the imaged portion of the innput screen 48, which constitutes the image receptor 46, is reduced in size.

From the foregoing description, it may be seen that only the X-radiation impinging on the imaged portion of the input screen assembly 48 is useful in forming the visible image on the output screen of image intensifier tube 50. Consequently, if the cross-sectional area of X-ray cone 30, at the plane of the image receptor 46, is greater than the area of the imaged portion of the input screen, the patient 44 is exposed to unnecessary radiation. Therefore, in order to protect the patient 44 from such overexposure to X-radiation, it is required that the cross-sectional area of the X-ray cone 30 conform closely to the useful area of the image receptor 46. From FIGS. 1 and 2, it may be seen that the cross-sectional size of X-ray cone 30, at the image receptor 46, is proportional to the diametric size of aperture 34 in beam-limiting device 32. Thus, the aperture 34 may be adjusted, as by knob 40, for example, to provide the X-ray cone 30 with the desired cross-sectional size. However, it has been found in a survey conducted by the United States Public Health Service that operators of this type of X-ray equipment tend to adjust knob 40 in a direction which will provide an X-ray cone having a cross-sectional area greater than the area of the image receptor. Consequently, in the practice of this invention, the knob 40 is reserved for use only during special diagnostic procedures by highly skilled personnel, and automatic means are provided for adjusting the cross-sectional size of X-ray cone 30 during routine diagnostic procedures.

Therefore, in accordance with this invention, the image intensifier tube 50 is supported in a suitable holder 60 having operably mounted thereon a receptor detecting means, such as a pressure actuated switch 62, for example. One side of switch 62 is connected to the positive side 64 of a suitable polarized voltage source (not shown), and the other side of switch 62 is connected, by means of a wire lead 66, to a collimator monitoring unit 68. Consequently, when an image intensifier tube, such as 50, for example, is inserted into the holder 60, pressure actuated switch 62 will be closed thereby sending an electrical signal through wire lead 66 to the collimator monitoring unit 68. Thus, the electrical signal produced by the receptor detecting means indicates that an image receptor is installed in position for receiving a radiation image of the subject 42.

The holder 60 is supported by a telescopic suspension post 70 on which there is mounted the remote control unit 71 and an attached receptor size sensing means, such as a potentiometer 72, for example. Potentiometer 72 includes a conventional resistive element 74 having one end connected to a positive terminal 78 of a polarized voltage source (not shown), and the other end connected to electrical ground. Thus, there is established along the resistive element 74 a graduated series of voltage value which may be sensed sequentially by a rotatable wiper arm 76. The arm 76 may be mechanically coupled to the control knob 73. As a result, the remote control knob 73 positions the wiper arm 76 on the resistive element 74 to sense a particular voltage value which is related to the diametric size of the imaged portion of the input screen 48. However, since there is a corresponding relationship between the respective diametric sizes of the imaged portion of the input screen 48 and the image receptor 46, the particular voltage value sensed by wiper arm 76 also may be correlated to the diametric size of image receptor 46. In this manner, the graduated series of voltage values established along resistive element 74 may be calibrated to indicate corresponding image receptor sizes, which are selected by adjusting control knob 73. Accordingly, the voltage value sensed by wiper arm 76 constitutes an electrical signal which is indicative of the diametric size of image receptor 46 and which is conducted through a connecting wire lead 80 to the collimator monitoring unit 68.

The telescopic suspension post 70 suspends from one end of an overhead carriage assembly 82 having a pair of spaced parallel rails 84 along which a support block 86 is movable in a conventional manner. The block 86 is attached to one end of a second telescopic suspension post 88 which extends between the rails 84, in spaced relation therewith, and is attached at the opposing end to housing 33 of beam-limiting device 32. Thus, moving the block 86 along the rails 84 carries the beam-limiting device 32 and attached X-ray generator 12 toward or away from the input screen 48 of image intensifier tube 50. As a result, the cross-sectional area of X-ray cone 30 at the plane of input screen 48 decreases or increases, respectively, in diametric size. Consequently, when adjusting the cross-sectional area of X-ray cone 30 to conform to the diametric size of input screen 48, a determination must be made of the distances between the focal spot 21 in X-ray generator 12 and the input screen 48 of image intensifier tube 50, which may be referred to as the "source-to-image receptor distance" or simply as "SID".

Therefore, in order to obtain an accurate measurement of the SID, one end of a cable 90 is fixedly attached to support block 86 by any convenient means, as by securing it to a pin 87 carried on block 86, for example. Cable 90 extends along the carriage assembly 82 and is wound around a spring loaded pulley 92 in a well-known manner. Thus, when the X-ray generator 12 is moved toward or away from the image intensifier tube 50, the cable 90 is respectively wound onto or drawn from the pulley 92. The resulting rotation of pulley 92 turns an axial shaft 94 which carries adjacent one end thereof a fixedly attached disc 96. The periphery of disc 96 is provided with a plurality of regularly spaced teeth 98 which sequentially engage a spring biased arm of an interrupter switch 100 thereby causing the switch 100 to open and close at regular intervals. One side of switch 100 is connected to a positive terminal 102 of a polarized voltage source (not shown), and the other side of switch 100 is connected through switches 122 and 124 and wire lead 104 to the collimator monitoring unit 68. Thus, switch 100, 122 and 124 constitutes an SID detecting means which produces an electrical signal indicative of a selected SID and interrupts the signal when the SID is changing.

The shaft 94 is operatively connected to a rotatable drum 106 which carries on its outer periphery a series of irregularly spaced landings 108, each of which engages a spring biased arm of a respective switch 110. Closing one of the switches 110 sends an electrical current through a respective series connected lamp 112 thereby illuminating the lamp to indicate that a particular SID value is selected. For example, standard radiographic procedures generally require the selection of one of four conventional SID values, namely 36 inches, 40 inches, 48 inches, and 72 inches, respectively. Thus, each of the landings 108 is precisely positioned on the periphery of drum 106 to light a respective lamp 112 and indicate the associated SID to within the required degree of accuracy. However, the landings 108 may be positioned on the periphery of drum 106 to indicate other SIDs, if desired. Also, more than the four landings 108 may be carried by the drum 106 to indicate respective SID values in addition to the conventional SID values generally selected.

The axial shaft 94 of pulley 92 also is mechanically coupled to a wiper arm 118 of a potentiometer 116 whereby turning of the shaft 94 results in rotating the wiper arm 118 correspondingly. The wiper arm 118 slidingly engages a conventional resistive element 120 having one end connected to wire lead 104 and through normally closed switches 122 and 124 to the positive terminal 102 of a polarized voltage source (not shown). The other end of resistive element 120 is connected to electrical ground. As a result, there is established along the resistive element 120 a graduated series of voltage values which are calibrated to correspond accurately to associated SID values. Consequently, when the shaft 94 positions the wiper arm 118 on the resistive element 120, the wiper arm 118 senses a particular voltage value which corresponds accurately to the SID selected. Thus, the potentiometer 116 constitutes an SID sensing means for producing an electrical signal indicative of a selected source-to-image receptor distance.

However, if the block 86 is moved along the rails 84 beyond a maximum SID limit, such as 80 inches, for example, the wiper arm 118 carries a dielectric cam member 126 which opens the switch 122 thereby preventing current flow through the resistive element 120 and the wire lead 104. Similarly, if the block 86 is moved along rails 84 to within a minimum SID limit, such as 30 inches, for example, the cam member 126 opens switch 124 thereby preventing current flow through the resistive element 120 and wire lead 104. These switches 122 and 124 constitute at least in part limiting means for preventing the emission of X-radiation, in the automatic mode, when the generator 12 is too far from or too close to the patient 44.

Mounted in the housing 33 of beam-limiting device 32 is a potentiometer 130 having a conventional resistive element 132 which is connected at one end to electrical ground. The other end of resistive element 132 is connected by means of wire lead 128 to the wiper arm 118 of potentiometer 116. Thus, the voltage value sensed by the wiper arm 118 is applied across the resistive element 132 of potentiometer 130. The resistive element 132 is slidably engaged by a wiper arm 134 which is operatively connected to ring 38 for rotation therewith when shutter aperture 34 is being adjusted, as previously described. In this manner, the wiper arm 134 senses the size of shutter aperture 34 and is positioned accordingly on the resistive element 132. Since the voltage applied across the resistive element 132 corresponds to a selected SID within the allowed range set by switches 122 and 124, respectively, the wiper arm 134 senses a particular voltage value which corresponds to the field size associated with the selected SID, as provided by the size of the shutter aperture 34. Thus, the potentiometer 130 constitutes a shutter aperture sensing means which in conjunction with the SID sensing means produces an electrical signal indicative of the radiation field size at the plane of the image receptor when the SID is within the allowed range. This electrical signal is fed through a connecting wire lead 136 to the collimator monitoring unit 68.

Figure 3:
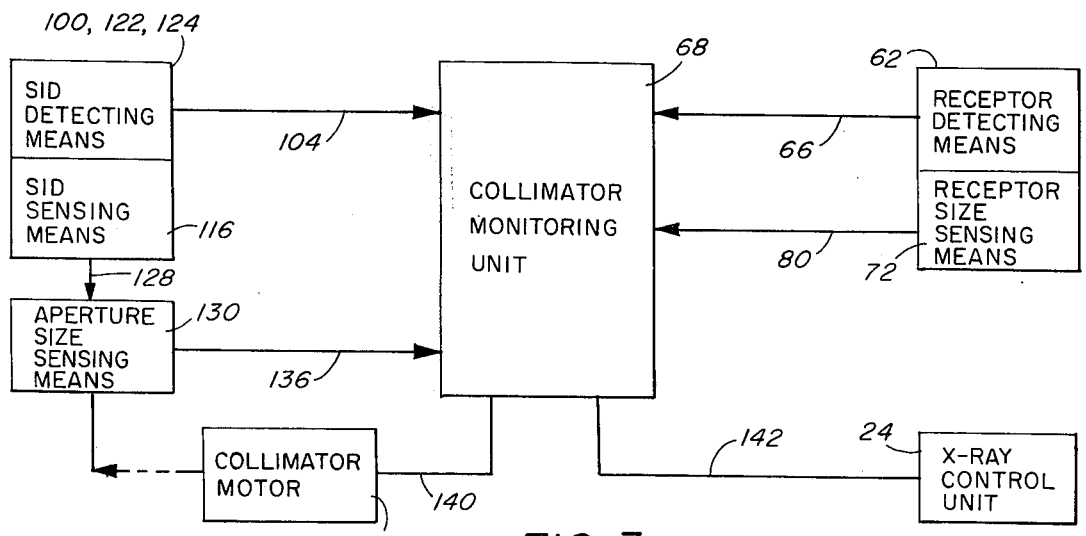
FIG. 3 is a block diagrammatic view of the basic components required for practicing this invention in conjunction with the system shown in FIG. 1.

Also mounted in the housing 33 of beam-limiting device 32 is a reversible motor 138 having a drive shaft 139 suitably geared to rotate the ring 38 and thereby adjust the shutter aperture 34. The motor 138 is energized by an electrical signal conducted through a wire lead 140 from the collimator monitoring unit 68. Thus, as shown in FIG. 3, the collimator monitoring unit 68 receives constant value voltage signals from the receptor detecting means 62 and the SID detecting means 100, 122 and 124 respectively. The collimator monitoring unit 68 also receives variable value voltage signals from the receptor size sensing means 72 and the radiation field size sensing means, 130 in conjunction with 116, respectively. From these input signals, the collimator monitoring unit 68 generates an electrical signal which drives the motor 138 in the proper direction for adjusting the shutter aperture 34 as required. While the shutter aperture 34 is being adjusted, the field size sensing means is adjusted accordingly, thus completing a servo loop. However, adjustment of the shutter aperture 34 must be completed before X-ray cone 30 is generated in order to protect the patient 44 from exposure to excess radiation. Therefore, the collimator monitoring unit 68 sends an electrical signal through a connecting wire lead 142 to the X-ray control unit 24 for the purpose of preventing generation of X-ray cone 30 until the shutter aperture 34 is completely adjusted.

Figure 4:
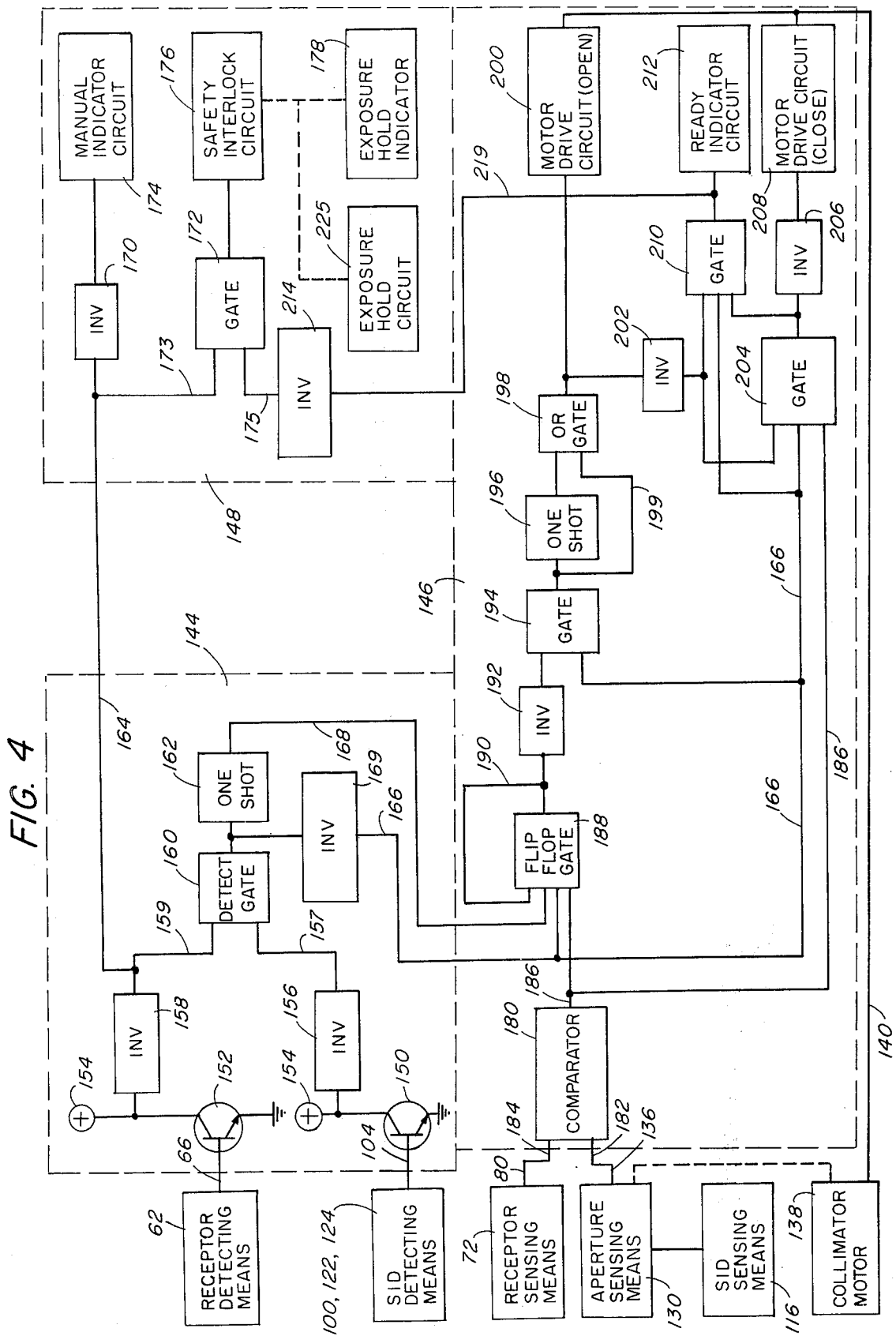
FIG. 4 is a block diagrammatic view of the invention as adapted for the system shown in FIG. 1.

As shown in FIG. 4, the collimator monitoring unit 68 includes a detector monitoring circuit 144, a sensor monitoring circuit 146, and an indicator/interlock circuit 148.

The detector monitoring circuit 144 may include two input transistors 150 and 152, respectively, the base of transistor 150 being connected to the SID detecting means 100, 122 and 124; and the base of transistor 152 being connected to the receptor detecting means 62. The transistors 150 and 152 have their respective emitters connected to electrical ground and their respective collectors connected to a source 154 of positive potential. The collector of transistor 150 is connected to an SID inverter 156 which has its output connected to an input lead 157 of a detector gate 160. Similarly, the collector of transistor 152 is connected to a receptor inverter 158 which has its output connected to an input lead 159 of detector gate 160.

The output of receptor inverter 158 also is applied to a conductor 164 which extends into the indicator/interlock circuit 148 to connect to the input of a manual indicator inverter 170 and also to an input lead 173 of a safety interlock gate 172. Thus, the conductor 164 constitutes one output lead of the detector monitoring circuit 144. The output of detector gate 160 is connected to the input of a one-shot multivibrator 162, and through an inverter 169 to a conductor 166 which constitutes a second output lead of the detector monitoring circuit 144. The output of the one-shot multivibrator 162 is applied to a conductor 168 which constitutes a third output lead of the detector monitoring circuit 144.

The sensor monitoring circuit 146 is provided with an input comparator 180 having input leads 182 and 184, respectively. The lead 182 is connected to the wiper arm 134 of the shutter aperture sensing potentiometer 130 through wire lead 136 and the lead 184 is connected to the wiper arm 76 of receptor size sensing potentiometer 72 through wire lead 80. Thus, an electrical signal indicative of the radiation field size at the selected SID is applied to the lead 182, when the selected SID is within the allowed range. Similarly, an electrical signal indicative of the diametric size of image receptor 46 is applied to the lead 184. These two signals are compared electrically in the comparator 180; and if one signal is larger than the other, an electrical signal corresponding to the difference between the two signals is applied to an output lead 186 of comparator 180.

The output lead 186 of comparator 180 and the output leads 166 and 168, respectively, of the detector monitoring circuit 144 are connected to the input of a flip-flop gate 188 having a latching feedback loop 190. The output of the flip-flop gate 188 is connected to the input of a sequencing inverter 192 which has its output connected to an input terminal of a sequencing gate 194. A second input terminal of the sequencing gate 194 is connected to the output lead 166 of detector monitoring circuit 144. The output of sequencing gate 194 is connected to the input of an overshoot, one-shot multivibrator 196 and through a lead 199 to the input of an open drive OR gate 198. The output of OR gate 198 is connected to the input of a motor drive circuit (open) 200, and also to the input of a ready indicator inverter 202.

The output lead 186 of comparator 180 and the output lead 166 of detector monitoring circuit 144 also are connected to respective input terminals of a close drive gate 204. A third input terminal of close drive gate 204 is connected to the output of ready indicator inverter 202 and to an input terminal of a ready indicator gate 210. The output of close drive gate 204 is connected to the input of a close drive inverter 206 and to a second input terminal of ready indicator gate 210. The output of close drive inverter 206 is connected to the input of a motor drive circuit (close) 208.

A third input terminal of ready indicator gate 210 is connected to the output conductor 166 of detector monitoring circuit 144. The output of ready indicator gate 210 is connected to the input of a ready indicator circuit 212 and through a conductor 219 to the input of a ready interlock inverter 214. The output of inverter 214 is connected through lead 175 to a second input terminal of safety interlock gate 172. The output of safety interlock gate 172 is connected to the input of a safety interlock circuit 176 which, in turn, activates an exposure hold indicator circuit 178 and an exposure hold circuit 225.

Figure 5:
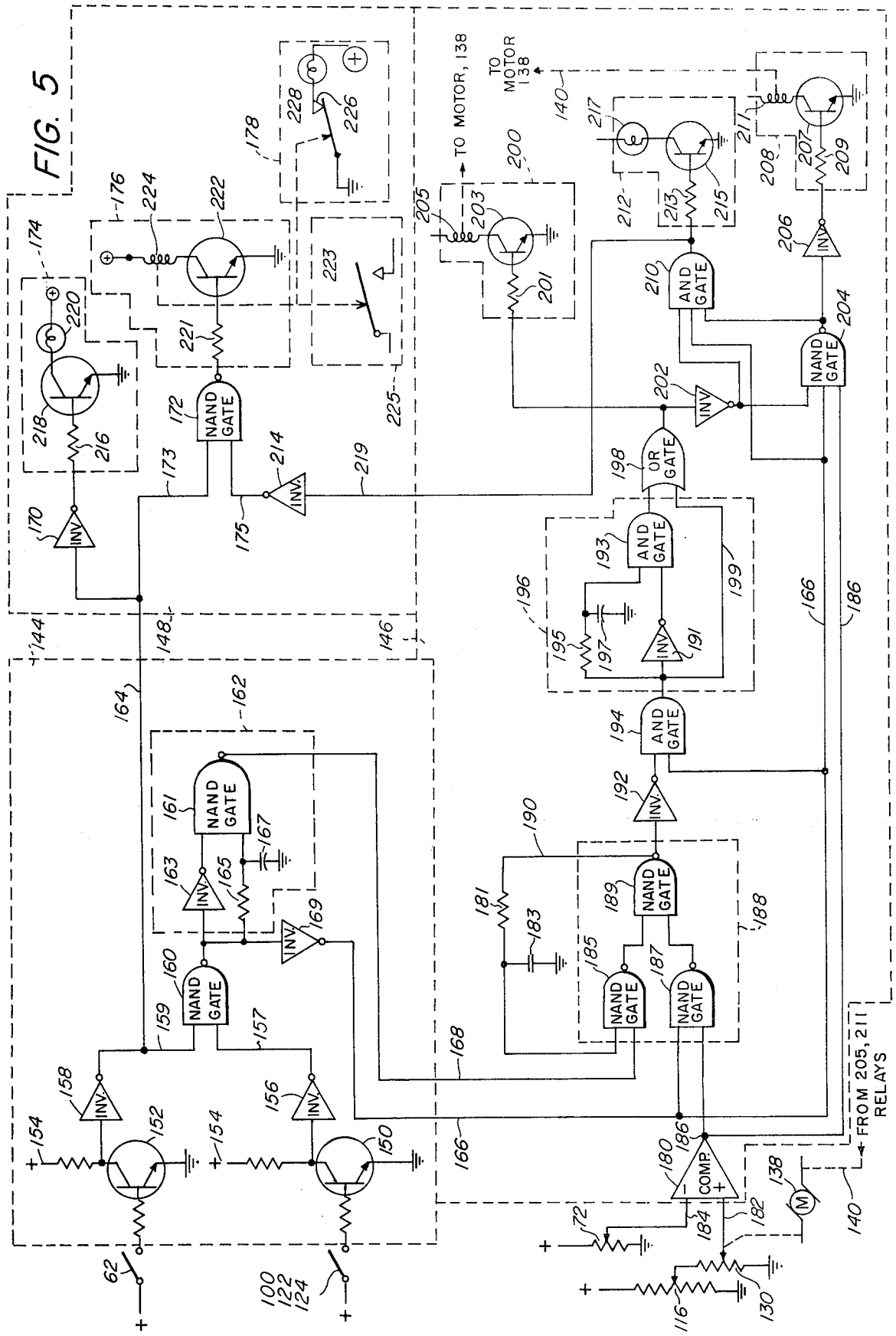
FIG. 5 is a schematic diagrammatic view of a typical embodiment of the invention as shown in FIG. 4.

A typical embodiment of the circuits shown in FIG. 4 is provided in FIG. 5 for purposes of illustrating this invention and utilizes conventional devices which are readily available on the commercial market.

Thus, in operation, when an SID is selected, the SID detecting switch means 100, 122, 124 send a constant value voltage signal to the base of transistor 150 thereby rendering it conductive and connecting the collector of transistor 150 to ground. The resulting drop to zero potential at the input of SID inverter device 156 causes it to send a logic One signal through the lead 157 to an input terminal of a detector Nand gate 160. However, the Nand Gate 160 does not produce a readiness output signal until a similar logic One signal is received at its other input terminal from the receptor inverter device 158.

If an image receptor is not in position to receive a radiation image, the receptor detecting switch 62 will not be closed to send a constant value voltage signal to the base of transistor 152. Consequently, transistor 152 will remain nonconductive, and the potential of source 154 will be applied to the input of receptor inverter device 158. As a result, the inverter device 158 will send a logic Zero signal through the lead 159 to the connected input terminal of detector Nand gate 160 which, accordingly, will not produce an output readiness signal. However, the logic Zero signal produced by the inverter device 158 also will flow through the output lead 164 to the manual indicator inverter 170 in the indicator/interlock circuit 148. Therefore, the inverter 170 will produce a logic One signal which will flow through a load resistor 216 to the base of a transistor 218 in the "Manual Operation" indicator 174. Consequently, the transistor 218 will conduct and thereby illuminate a Manual Operation indicator lamp 220.

The logic Zero signal applied to the input of inverter 170 also will pass through lead 173 to an input terminal of a safety interlock Nand gate 172. As a result, the Nand gate 172 will produce at its output a logic One signal which will be applied through a load resistor 221 to the base of a transistor 222 in the safety interlock circuit 176. Accordingly, the transistor 222 will be rendered conductive and permit current to flow through a series connected relay coil 224. Consequently, an "exposure hold" circuit 225 will be completed by the closing of relay contacts 223 thereby allowing X-ray exposures to be taken in the manual mode of operation. Relay contacts 226 also open, thereby extinguishing the "Exposure Hold" indicator lamp 228. Thus, this invention provides means for automatically returning system 10 to a manual mode of operation and allowing X-ray exposures to occur when an image receptor is not in position for automatic operation.

If, however, an image receptor is supported in the holder 60, the receptor detector switch 62 will be closed and will apply a constant value voltage signal to the base of transistor 152. Accordingly, the transistor 152 will be rendered conductive thereby connecting the collector of transistor 152 to ground. The resulting drop to zero potential at the input of receptor inverter 158 will cause it to send a logic One signal to the input of the manual indicator inverter 170 and through lead 173 to the safety interlock Nand gate 172. Consequently, the inverter 170 will produce a logic Zero signal which will render transistor 218 non-conductive and extinguish the "Manual Operation" indicator lamp 220. The logic One signal applied to the input of inverter 170 also will be applied through lead 173 to the connected input terminal of safety interlock Nand gate 172. Consequently, when the other input lead 175 of Nand gate 172 is at a logic One, the Nand gate 172 will produce a logic Zero signal which will render transistor 222 non-conductive and deenergize relay coil 224. Accordingly, the "exposure hold" circuit will be actuated by the opening of relay contacts 223 and X-ray emission will be prevented by the collimator monitoring unit 68. Relay contacts 226 also close thereby illuminating the "Exposure Hold" indicator lamp 228.

The output of detector Nand gate 160 is connected to an inverter 169 which is connected in series with the output lead 166 of the detector monitoring circuit 144. The output of detector Nand gate 160 also is connected in series with an inverter 163 which is connected to an input terminal of a Nand gate 161. A second input terminal of Nand gate 161 is connected to the positive side of a capacitor 167 having a negative side connected to ground, and also is connected through a resistor 165 to the output of detector Nand gate 160. Thus, with no image receptor in position, the resulting logic Zero signal applied to the input lead 159 causes Nand gate 160 to produce at its output a logic One signal. As a result, the inverter 169 applies a logic Zero signal to the output lead 166, and the inverter 163 applies a logic Zero signal to the connected input terminal of Nand gate 161. Also, the logic One signal at the output of Nand gate 160 will be applied through resistor 165 directly to the other input terminal of Nand gate 161 and will charge the capacitor 167 to a logic One voltage value.

Then, when an image receptor is installed in the holder 60, the resulting logic One signal applied to lead 159 in conjunction, with the logic One signal to lead 157 causes the Nand gate 160 to change its output signal from logic One to logic Zero. As a result, the inverter 169 applies a logic One signal to the output lead 166, and the inverter 163 applies a logic One signal to the connected input terminal of Nand gate 161. However, the capacitor 167 maintains the other input terminal of Nand gate 161 at the stored logic One signal also for the time required to discharge the stored signal through the resistor 165. Thus, for the RC time of the resistor 165 and capacitor 167 network, both input terminals of Nand gate 161 will have a logic One signal. Consequently, during that short interval of time the output of Nand gate 161 will drop to a logic Zero and then will return to a logic One when capacitor 167 has discharged to a logic Zero voltage value. Accordingly, whenever an image receptor is changed and an SID is selected, the Nand gate 161 will produce a negative going pulse at its output. The timed pulse produced by Nand gate 161 will be applied to output lead 168 of the detector monitoring circuit 144.

The flip-flop gate 188 comprises two Nand gates 185 and 187, respectively, which have their outputs connected to respective input terminals of a third Nand gate 189. Flip-flop 188 is latched in one of two operating conditions by latching loop 190 which connects the output of Nand gate 189 through a series resistor 181 to an input terminal of Nand gate 185 and also to the positive side of a capacitor 183 having its negative side connected to ground. The flip-flop 188 is pulsed momentarily by the negative going pulse applied to output lead 168 which is connected to the other input terminal of Nand gate 185. When thus pulsed, the operating condition of flip-flop 188 is determined by the electrical signal applied to comparator output lead 186 which is connected to one of the input terminals of Nand gate 187. The other input terminal of Nand gate 187 is connected to the output lead 166 which has a constant logic One signal applied to it when an image receptor is in position and an SID is selected.

If the receptor size signal at the input lead 184 of comparator 180 is larger than the field size signal at the input lead 182, the output lead 186 will have applied to it an electrical signal which is equivalent to a logic Zero and indicates that the shutter aperture 34 should be opened. As a result, the Nand gate 187 will produce at its output a logic One signal. Also, while the negative going pulse applied to output lead 168 is at a logic Zero level, the Nand gate 185 will produce at its output a logic One signal. Thus, with both input terminals of Nand gate 189 at logic One, it produces at its output a logic Zero signal which will be applied to the connected input terminal of Nand gate 185. Consequently, the output of Nand gate 185 will be maintained at logic One even when the negative going pulse in lead 168 returns to a steady logic One value. Therefore, the flip-flop device 188 is latched in an operating condition which permits opening of the shutter aperture 34.

The latched logic Zero signal at the output of the flip-flop 188 causes the sequencing inverter 192 to send a logic One signal to the connected input terminal of a sequencing And gate 194. The function of And gate 194 is to determine whether the flip-flop 188 has been unlatched and allowed to flip to a shutter opening operative condition due to a transient pulse from some other source, such as a momentary power failure, for example. Consequently, the other input terminal of And gate 194 is connected to the output lead 166 of detector monitoring circuit 144 to insure that an image receptor is in position and an SID has been selected. Therefore, with a logic One signal on each of its input terminals, the And gate 194 will produce at its output a logic One signal.

Thus, it may be seen that the values of resistor 181 and capacitor 183 are selected to provide an RC time constant longer in duration than any expected transient pulse in order to avoid unintended unlatching of the flip-flop 188 and a consequent undesirable opening of the shutter aperture 34. Typical values selected for the resistor 181 and capacitor 183 are 330 ohms and 150 microfarads, respectively, to provide an RC time constant of approximately 50 milliseconds. Therefore, the values of resistor 165 and capacitor 167 in the detector monitoring circuit are selected to provide an unlatching pulse of longer time duration than the RC time constant of resistor 181 and capacitor 183. Accordingly, typical values selected for resistor 165 and capacitor 167 may be 330 ohms and 200 microfarads, respectively, to provide a pulse duration of approximately 65 milliseconds.

The overshoot one-shot multivibrator 196 comprises an And gage 193 having one input terminal connected through an inverter 191 to the output of sequencing And gate 194, and another input terminal connected to the positive side of a capacitor 197 and through a resistor 195 to the output of sequencing And gate 194, the negative side of capacitor 197 being connected to ground. Thus, the logic One output signal produced by sequencing And gate 194 charges the capacitor 197 accordingly and is applied to the connected input terminal of And gate 193. The same logic One signal at the input of inverter 191 causes it to apply a logic Zero signal to the other input terminal of And gate 193. Thus, with a logic One and a logic Zero signals at its respective input terminals, the And gate 193 applies a logic Zero signal to a connected input terminal of open-drive Or gate 198.

However, the logic One signal produced by sequencing And gate 194 also is applied through a by-pass lead 199 to the other input terminal of Or gate 198. As a result, the Or gate 198 sends a logic One signal through a load resistor 201 in motor drive circuit 200 to the base of a transistor 203 thereby rendering it conductive. Consequently, current will flow through a relay coil 205 which energizes the motor 138 in the housing 33 of beam-limiting device 32. Accordingly, the motor 138 will rotate ring 38 to pivot the shutter leaves 37 into lesser overlapping relationship thereby opening the shutter aperture 34. Since the rotation of ring 38 also moves the wiper arm 134 slidingly along the resistive element 132 of aperture size sensing potentiometer 130 correspondingly until the field size signal applied to the input lead 182 of comparator 180 equals the receptor size signal applied to input lead 184. As a result, the electrical signal applied to output lead 186 of comparator 180 will change from logic Zero to logic One.

When the electrical signal applied to output lead 186 of comparator 180 has changed to logic One, the flip-flop device 188 will change it to its other operating condition and will produce an output logic One signal at the input of sequencing inverter 192. The flip-flop device 188 will be latched in this operating condition. The logic One signal at the output of flip-flop device 188 will cause the inverter 192 to send a logic Zero signal to the connected input terminal of sequencing And gate 194. Consequently, the And gate 194 will produce at its output a logic Zero signal which will cause the inverter 191 to apply a logic One signal to the connected input terminal of overshoot And gate 193. Since the capacitor 197 is charged to a logic One signal, both input terminals of the And gate 193 will be at a logic One during the discharge time of capacitor 197. Consequently, the And gate 193 will apply a logic One signal to the connected input terminal of Or gate and cause it to continue to apply a logic One signal to the base of transistor 203, even though the other input terminal of Or gate 198 is now at logic Zero.

As a result, the motor 138 will continue to pivot the shutter leaves 37 and the aperture 34 will open beyond the corrective adjustment required initially by the comparator 180. Accordingly, the ring 38 will slide the wiper arm 134 along the resistive element 132 to produce at the input lead 182 of comparator 180 a field size signal which is larger than the receptor size signal. Therefore, the electrical signal applied to output lead 186 will remain at a logic One which indicates that the shutter aperture should be closed down. The logic One signal applied to output lead 186 will not affect the output of flip-flop device 188 which will remain latched with a logic One output. Consequently, when the capacitor 197 is discharged, the overshoot And gate 193 will produce at its output a logic Zero signal. Thus, with both inputs of the Or gate 198 at logic Zero, it will apply a logic Zero to the base of transistor 203 thereby rendering it non-conductive and stopping motor 138.

The logic Zero signal produced by Or gate 198 will cause the connecting close drive inverter 202 to apply a logic One signal to the connected input terminal of close drive Nand gate 204. A second input terminal of Nand gate 204 is connected to output lead 186 which is at a logic One. A third input terminal of Nand gate 204 is connected to output lead 166 which also is at a logic One thereby insuring that an image receptor is in position and an SID is selected. Consequently, with logic One signals on all three input terminals of the Nand gate 204, it will apply a logic Zero signal to the input of inverter 206, which, accordingly, will apply a logic One signal through a load resistor 209 to the base of a transistor 207 in the motor drive circuit (close) 208. As a result, current will flow through a relay coil 211 which will energize motor 138 to rotate the ring 38 and pivot the shutter leaves into greater overlapping relationship thereby closing the aperture 34.

The coresponding movement of wiper arm 134 along resistive element 132 will produce at the input lead 182 of comparator 180 a field size signal which will be equal in magnitude to the receptor size signal applied to input lead 184. Consequently, the electrical signal applied to output lead 186 will change to a logic Zero which will be applied to the connected input terminal of Nand gate 204. As a result, Nand gate 204 will send a logic One signal to inverter 206 which will apply a logic Zero signal to the base of transistor 209 thereby rendering it non-conductive. Thus, relay coil 211 will be deenergized and the motor 138 will stop.

The logic Zero signal now applied to output lead 186 is prevented from changing the flip-flop 188 to a shutter opening operative condition by the absence of an unlatching pulse from the one-shot multivibrator 162 in the detector monitoring circuit 144. Consequently, the flip-flop 188 will remain latched in a shutter closing operative condition which permits further closing of the shutter aperture 34 by manually adjusting knob 40. However, any attempt to open the shutter aperture 34 beyond the diametric size of image receptor 46, as by knob 40, for example, will move the wiper arm 134 along resistive element 132 of aperture size sensing potentiometer 130. As a result, the field size signal applied to input lead 182 of comparator 180 will become larger in magnitude than the receptor size signal applied to input lead 184. Accordingly, the electrical signal applied to output lead 186 of comparator 180 will change from logic Zero to logic One which will be applied to the connected input terminal of Nand gate 204 and result in the motor 138 closing the shutter aperture 34 down to its automatically set dimension, as previously described. Consequently, the field size signal applied to input lead 182 of comparator 180 again will equal the receptor size signal on input lead 184, and the electrical signal applied to output lead 186 will change from logic One to logic Zero.

The logic Zero signal applied to output lead 186 of comparator 180 will be delivered to the connected input terminal of Nand gate 204. Consequently, Nand gate 204 will produce at its output a logic One signal which will be sent to a connected input terminal of ready indicator And gate 210. As stated previously, the Or gate 198 will have at its output a logic Zero signal which will result in an inverter 202 applying a logic One signal to a second connected input terminal of ready indicator And gate 210. Also, the output lead 166 of detector monitoring circuit 144 will apply a third logic One signal to a connected input terminal of ready indicator And gate 210, thereby insuring that an image receptor is in position to receive an X-ray image and that an SID has been selected. Thus, with logic One signals on all three of its terminals, the And gate 210 will apply a logic One signal through a load resistor 213 to the base of a transistor 217 in ready indicator circuit 212. Consequently, the transistor 217 will be rendered conductive thereby permitting current flow through the filament of a series connected lamp 212. As a result, the "Ready" indicator lamp 212 will be illuminated to signify that the shutter aperture 34 has been completely adjusted to limit an X-ray cone 30 to a crosssectional size which conforms to the diametric size of the image receptor 46.

The logic One signal produced at the output of ready indicator And gate 210 also will be applied through a conductor 219 to the input of a safety interlock inverter 214. As a result, inverter 214 will send a logic Zero signal through lead 175 to a connected input terminal of a safety interlock Nand gate 172. As stated previously a logic One signal on output lead 164 of detector monitoring circuit 144 will be applied through lead 173 to the other input terminal of Nand gate 172. Consequently, the Nand gate 172 will produce at its output a logic One signal which will be applied through a load resistor 221 to the base of a transistor 222 in safety interlock circuit 176. As a result, transistor 222 will be rendered conductive thereby permitting current flow through a relay coil 224, which will open contacts 226 in the "Exposure Hold" indicator 178 and will close contacts 223 in the "Exposure Hold" circuit 225. Thus, the "Exposure Hold" lamp 228 will be extinguished and the "Exposure Hold" circuit will be completed thereby permitting the emission of X-rays from the source 21 in X-ray generator 12.

The total elapsed time for completing the entire described cycle from the detection of an image receptor 46 and a selected SID to the release of an "Exposure Hold" on X-ray emission has been found to be in the range of approximately one-tenth of a second to approximately 1 second. Changing the image receptor or the SID causes the described beam-limiting system to recycle and open the shutter aperture 34 to the maximum allowed dimension. During a shutter opening cycle, the automatic system of this invention will open the shutter aperture to a size greater than the required dimension, because of an overshoot drive pulse supplied by the one-shot multivibrator 196 in the sensor monitoring circuit 148. Then, after stopping the drive motor 138, the beam-limiting system of this invention will close the shutter aperture 34 down to the correct dimension. During a shutter closing cycle, the automatic beam-limiting system of this invention will merely close the shutter aperture 34 down to the correct dimension. Thus, when adjusting the shutter aperture, the automatic system of this invention, causes the shutters to go through a unidirectional final adjustment whereby the shutters always approach the correct dimension from the same direction. In this manner, mechanical backlash, electronic lag and other forms of hysteresis are removed from the drive system when adjusting the shutter aperture 34. Consequently, the erroneous effects due to hysteresis are avoided. It has been found that a beam-limiting system embodying this invention can regulate the diametric size of the X-ray cone with respect to the area of the image receptor such that the sum total of all deviations regardless of sign is well within two percent of the SID.

Figure 6:
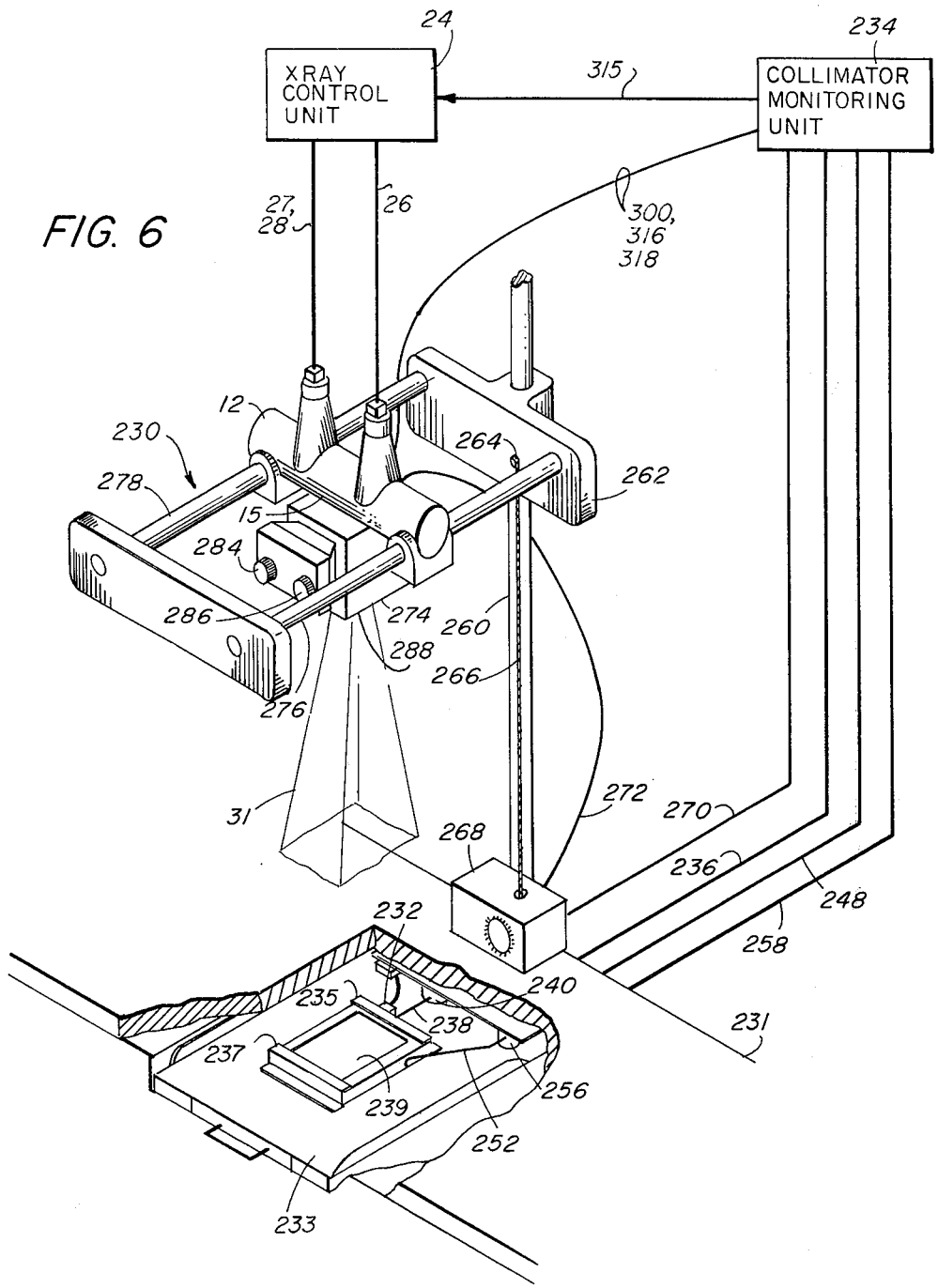
FIG. 6 is a perspective view of another type of radiographic system embodying the invention.
Figure 7:
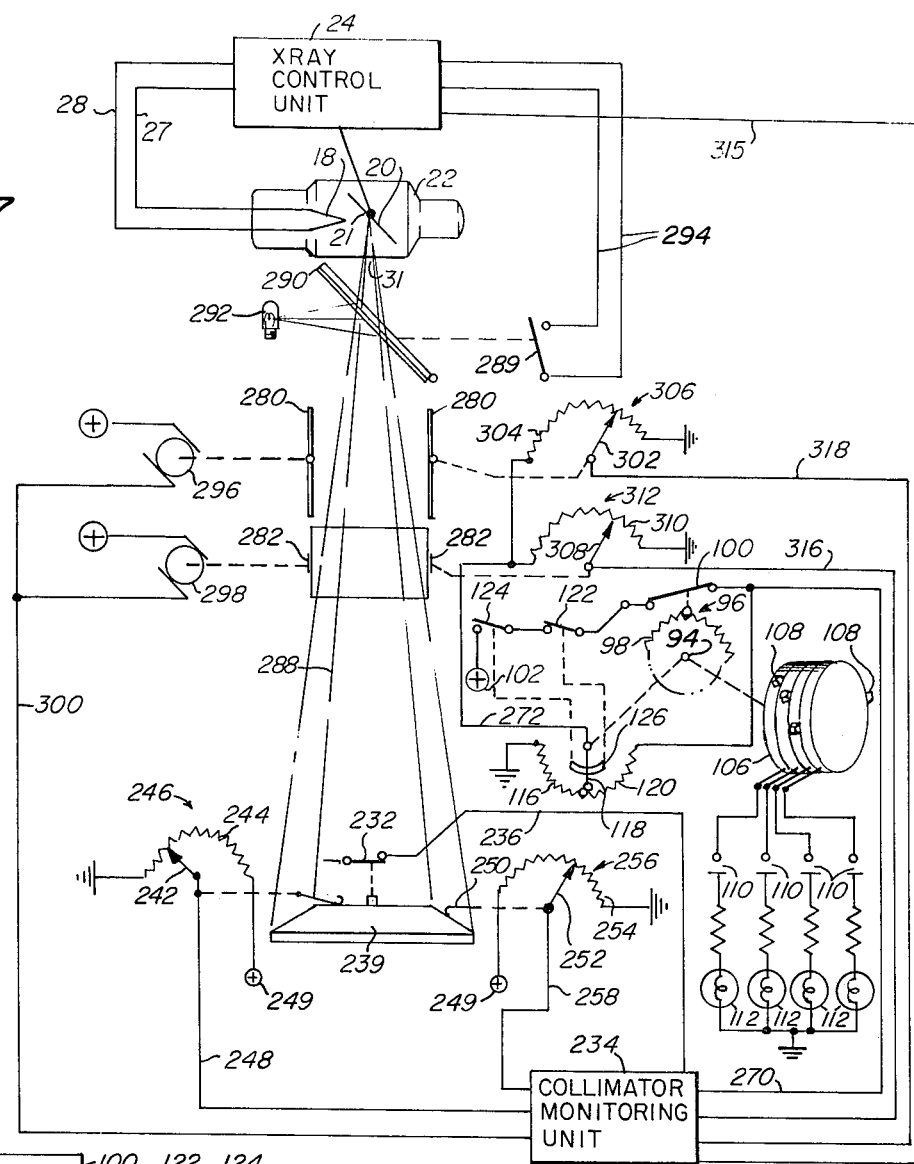
FIG. 7 is a schematic view of the radiographic system shown in FIG. 6.

It is to be understood however, that the automatic system of this invention is adaptable for use with other types of radiographic systems. There is shown in FIGS. 6 and 7, an X-ray system 230 comprising an X-ray table 231 whereon a patient (not shown) may be disposed for X-ray examination. Slidably inserted beneath the surface of table 231 is an image receptor holder comprising a tray 233 having on its upper surface opposing clamps 235 and 237 which are slidably mounted for simultaneous slidable movement toward and away from one another in a well-known manner.

An image receptor comprising a rectangular, film bearing cassette 239 is inserted between the clamps 235 and 237, respectively, and then the clamps are slidingly moved into abutting relationship with opposing edges of the cassette 239. The clamp 235 carries a pressure actuated switch 232 which is closed when the clamp 235 abuts the adjacent edge of cassette 239. Thus, the switch 232 constitutes a receptor detecting means which produces a constant value electrical signal indicative of the installation of an image receptor in the holder. This constant value electrical signal is fed to a collimator monitoring unit 234 by means of a connecting wire conductor 236.

A cable 238 is suitably attached at one end to the clamp 235 and is wound around a spring loaded pulley 240 which is rotatably mounted at the back of tray 233. Mechanically coupled to the pulley 240 for rotation therewith is a wiper arm 242 having an end portion which slidably contacts a resistive element 244 of a potentiometer 246. The resistive element 244 is connected at one end to a positive voltage source 249 and at the other end to electrical ground. Consequently, there is established along the resistive element a graduated series of voltage values which may be calibrated to correspond with the dimension of a cassette 239 held between the clamps 235 and 237. This dimension generally, is referred to as the "cross-table" or simply "cross" dimension of the cassette 239, the other orthogonal dimension of the cassette being referred to as the "longitudinal" or simply "long" dimension.

Although the clamps 235 and 237 do not abut respective edges the X-ray film in the cassette there is a corresponding relationship between the dimensions of the film and the dimensions of the cassette whereby the graduated voltage values established along the resistive element 244 can be correlated to the film sizes associated with respective cassette sizes. Thus, the potentiometer 246 constitutes a "cross" receptor sensing means which produces a variable electrical signal indicative of the "cross" dimension of the X-ray film in cassette 239. This electrical signal is fed to the collimator monitoring unit 234 by means of a wire conductor 248 having one end electrically connected to the wiper arm 242 and the other end connected into the collimator monitoring unit.

One end of a pivotal arm 250 lightly contacts a side edge of the cassette 239 and rotates a wiper arm 252 having an end portion slidably contacting a resistive element 254 of a potentiometer 256. The resistive element 254 is connected at one end to a positive voltage source 249 and at the other end to electrical ground. Thus, in a manner similar to that described for potentiometer 246, there is established along the resistive element 254 a graduated series of voltage values which may be calibrated to correspond to respective "long" dimensions of an X-ray film and which may be sensed by the slidable arm 252. Accordingly, the potentiometer 256 constitutes a "long" receptor sensing means which produces a variable electrical signal indicative of the "long" dimension of the X-ray film in cassette 239. This electrical signal is fed to collimator monitoring unit 234 through a wire conductor 258 having one end connected to the wiper arm 252 and the other end connected into collimator monitoring unit 234.

An upright support post 260 has extending outwardly therefrom a carriage assembly 262 which is mounted for slidable movement along the post 260, such that it can be moved toward and away from the table 231. Attached to the carriage assembly 262 by suitable means, as by pin 264, for example, is an end portion of a cable 266 which extends downwardly into a housing 268 mounted on the table 231. The cable 266 is wound around a spring-loaded pulley (not shown) in the well-known manner and rotates the pulley as the carriage assembly 262 is moved relative to the X-ray table 231. Mechanically coupled to the pulley for rotation therewith is an interrupter disc 94 having a plurality of teeth 96 on the periphery thereof whereby an interrupter switch 100 is intermittently closed and opened in a regular manner as the carriage assembly 262 is moved relative to the table 231. Thus the switch 100 constitutes an SID detecting means which produces an electrical signal indicative of a change in SID, as set forth in detail in the previously described embodiment. This electrical signal is fed to the collimator monitoring unit 234 through an interconnecting conductor 270.

Rotatable with the disc 100 is a drum 106 having disposed on the periphery thereof a series of irregularly spaced landings 108 which actuate respective switches 110 to illuminate respective lamps 112 which indicate when a respective SID value has been reached, as previously described. Also rotatable with the disc 100 is a wiper arm 118 having an end portion slidably contacting a resistive element 120 of a potentiometer 116. The resistive element 120 is connected at one end to a positive voltage source 102 and at the other end to electrical ground. Thus, as previously described, there is established along the resistive element 120 a graduated series of voltage values which may be calibrated to correspond to respective source-to-image receptor distances. The wiper arm 118 senses a particular value associated with a selected SID and delivers it through a conductor 272 to a beam-limiting device 274 which is mounted over the port 15 of X-ray generator 12.

The X-ray generator 12 is movably supported on rails 276 and 278 of the carriage assembly 262 such that the X-ray source 21 in generator 12 is aligned with the center of the film bearing cassette 239 in tray 233. The X-ray source 21 emits a conical beam 31 of X-radiation which egresses through port 15 and passes through the beam-limiting device 274. The device 274 comprises two orthogonically disposed pairs, 280 and 282, respectively, of opposing shutter plates. The plates 280 and 282 are made of X-ray absorbent material, such as lead, for example, and are pivotally mounted to move simultaneously toward and away from one another, as adjusted by respective control knobs 284 and 286, respectively, mounted on the exterior of the beam limiting device. Thus, the plates 280 limit the "long" dimension of a rectangular aperture 288 formed by the shutter plates and the plates 282 limit the "cross" dimension. In this manner, the conical beam 31 is provided with a rectangular cross-sectional area which, at the plane of the film bearing cassette 239, conforms to the area of the X-ray film in the cassette.

To align the source 21 with the center of the cassette 239, there is provided a visible light centering means comprising a mirror 290 centrally located on the axial centerline of the beam-limiting device 274 and disposed at an angle thereto so as to reflect visible light from a suitable source 292 through the rectangular aperture 288. The source 292 is located offaxis a sufficient distance to project by means of mirror 290 a virtual image which is optically located at the point source 21 of X-radiation. In this manner, it may be determined by the field of visible light at the plane of the cassette 239 whether the source 21 and beam-limiting device 274 are aligned with the cassette 239. Thus, it may be seen that the beam-limiting device 274 is suitable for collimating a beam of visible light as well as an X-ray beam.

The mirror 290 is left in place during an X-ray exposure in order to provide the required filtration of soft X-rays. However, it is pivotally mounted so as to be rotated off axis when necessary, such as to examine the X-ray emitting surface of anode 20, for example. Therefore, in order to insure that the mirror 290 is in position during an X-ray exposure, there is provided a pressure actuated switch 289 which is closed by the mirror 290 when it is rotated off axis. The switch 289 is connected by means of conductors 294 to the X-ray control unit 24 whereby X-ray emission will be delayed until the mirror 290 is rotated back into position for filtering out soft X-radiation.

In the practice of this invention, there is provided within the housing of beam-limiting device 274, two motors, 296 and 298, respectively, each of which functions in a manner similar to that of motor 138 in the previously described embodiment. Thus, the motor 296 pivots plates 280 toward and away from one another to automatically limit the "long" dimension of aperture 284; and the motor 298 rotates the plates 281 toward and away from one another to limit the "cross" dimension of aperture 288. The motors are electrically connected through a cable 300 to the collimator monitoring unit 234. Also, the motor 296 is mechanically connected to the wiper arm 302 of a "long" aperture sensing potentiometer 306 whereby rotation of the shaft of motor 296 to vary the "long" dimension of shutter aperture 288 also moves the wiper arm 302 correspondingly along a resistive element 304 of potentiometer 306. Similarly, the motor 298 is mechanically connected to the wiper arm 308 of a "cross" aperture sensing potentiometer 312 whereby rotation of the shaft of motor 298 to vary the "cross" dimension of shutter aperture 288 also moves the wiper arm 308 correspondingly along a resistive element 310 of potentiometer 312.

Since the particular voltage value indicative of the selected SID is impressed across the resistive elements, 304 and 310, respectively, there will be established along each of the resistive elements a graduated series of voltage values which may be calibrated to correspond to respective field size values at the plane of the selected SID. Thus, the wiper arm 302 will sense a particular voltage value indicative of the field size provided by the opening between "long" limiting shutter plates 280; and the wiper arm 308 will sense a particular voltage value indicative of the field size provided by the opening between "cross" limiting shutter plates 282. The wiper arms are connected electrically through respective conductors 316 and 318 to the collimator monitoring unit 234.

Figure 8:
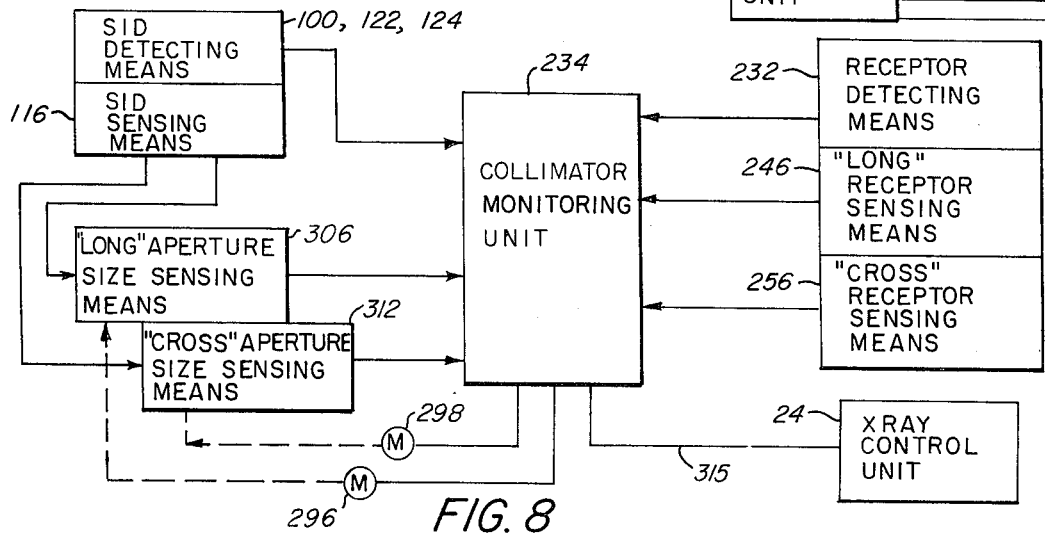
FIG. 8 is a block diagrammatic view of the basic components required for practicing this invention in conjunction with the system shown in FIG. 6.

Thus, as shown in FIG. 8, the collimator monitoring unit 234 will receive constant value voltage signals from the receptor switch detecting means 232 and from the SID switch detecting means 100, 122 and 124. The collimator monitoring unit 234 also will receive variable voltage signals from the "long" receptor sensing means 246, the "cross" receptor sensing means 256, the "long" aperture sensing means 306, and the "cross" aperture sensing means 312. With these signals, the collimator monitoring unit 234 generates an electrical signal to drive the "long" adjustment motor 296, and another electrical signal to drive the "cross" adjustment motor 298. In this manner, the shutter aperture 288 is automatically adjusted, prior to X-ray emission, to provide the X-ray beam with a rectangular cross-sectional size which, at the plane of the image receptor, conforms to the rectangular area of the X-ray film in cassette. However, in order to insure that a patient is not exposed to X-radiation before the aperture 288 is completely adjusted, the collimator monitoring unit 234 is connected through a conductor 315 to the X-ray control unit 24 whereby X-ray emission may be delayed until adjustment of the aperture 288 is completed.

Figure 9:
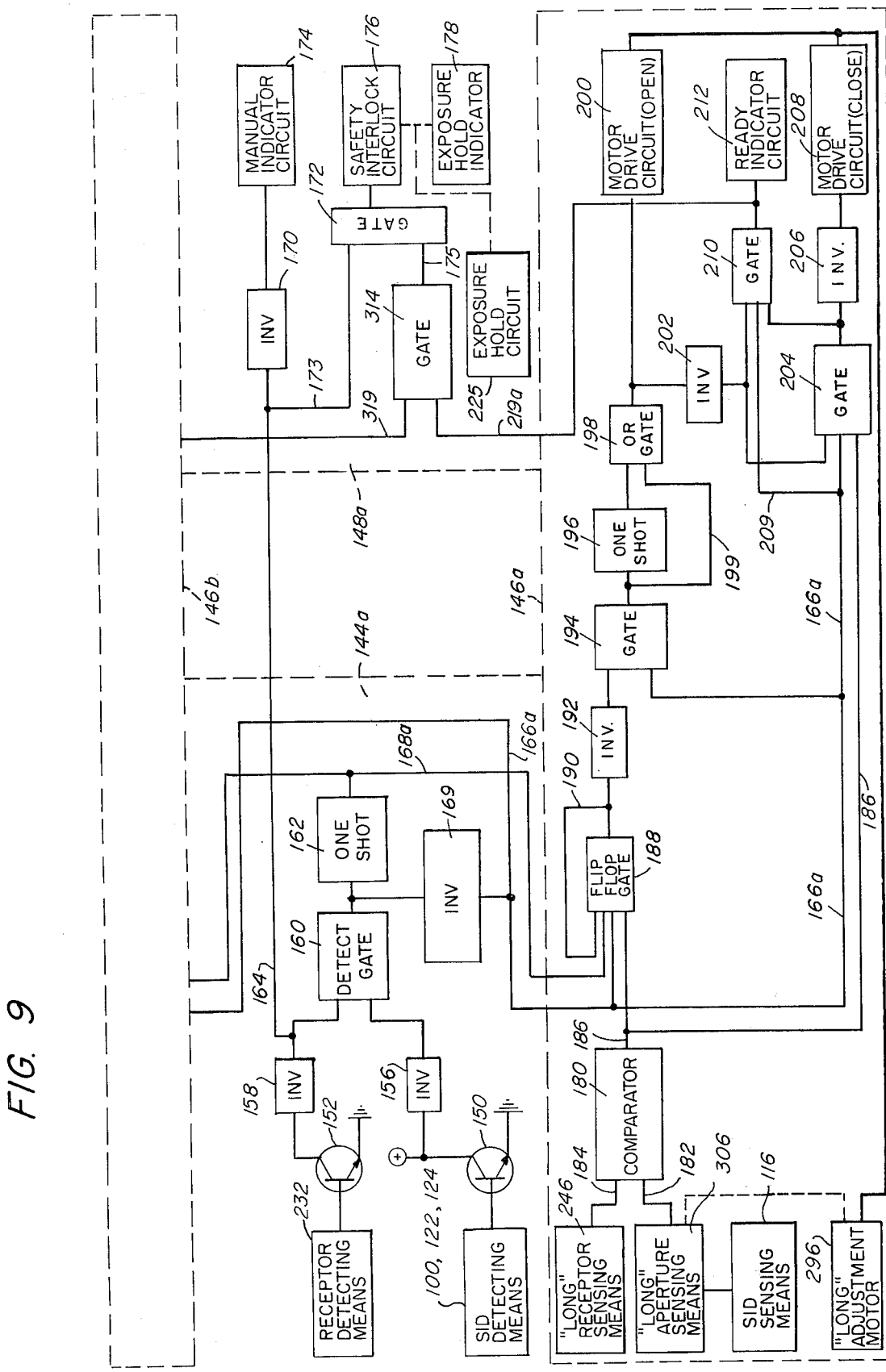
FIG. 9 is a block diagrammatic view of the invention as adapted for the system shown in FIG. 6.

As shown in FIG. 9, the "long" sensor monitoring circuit 146a is identical to the sensor monitoring circuit 146 described in the previous embodiment, and the "cross" sensor monitoring circuit, designated by block 146b, is identical to the circuit 146a. The detector monitoring circuit 144a is identical to the detector monitoring circuit 144 described in the previous embodiment, except the output leads 166a and 168a are connected to associated components in the two sensor monitoring circuits, 146a and 146b, respectively. The indicator/interlock circuit 148a is similar to indicator/interlock circuit 148 in the previous embodiment, except the safety interlock inverter 214 in the previous embodiment is changed to a ready interlock Nand gate 314 to provide means for determining when both the "long" and the "cross" shutter adjustments are completed.

An illustrative embodiment of the circuits shown in FIG. 9 is provided in FIG. 10 and utilizes conventional devices which may be of the integrated circuit type and may be mounted on a control panel of the printed circuit type, for example. A comparison of the illustrative embodiment shown in FIG. 5 with the illustrative embodiment shown in FIG. 10 indicates that the devices utilized to form circuit 144 are identical to the devices utilized to form circuit 144a. Similarly, the devices utilized to form circuit 146 are identical to the devices of circuit 146a and would be identical to the devices of circuit 146b if shown. Also, the devices utilized to form circuit 148 are identical to the devices utilized to form circuit 148a except the inverter 214 in circuit 148 is changed to a Nand gate 314 in circuit 148a, as previously described. Thus, the circuits 144a, 146a, 146b and 148a will function in a similar manner to that described for the illustrative embodiment shown in FIG. 5.

From the foregoing, it will be apparent that all of the objectives of this invention have been achieved by the structures shown and described. It will be also apparent, however, that various changes may be made by those skilled in the art without departing from the spirit of the invention as expressed in the appended claims. It is to be understood, therefore, that all matter shown and described is to be interpreted as illustrative and not in a limiting sense.

I claim:

1. A radiographic system comprising:
 means for directing an X-ray beam from a source through an adjustable shutter aperture and onto an image receptor located at a predetermined distance from the source; and
 automatic means for adjusting the shutter aperture to provide the X-ray beam with a cross-sectional size conforming to the image receptor at the predetermined distance from the source, the automatic means including source-to-image distance sensing means for producing an output electrical signal corresponding to the source-to-image receptor distance, and shutter aperture size sensing means connected to the outpput of the source-to-image distance sensing means for modifying said signal in accordance with a defining dimension of the actual shutter aperture size and producing an associated field size electrical signal corresponding to the actual radiation field size at the plane of the image receptor.

2. A radiographic system as set forth in claim 1 wherein the shutter aperture size sensing means includes signal divider means for converting the signal corresponding to the source-to-image receptor distance into a graduated series of voltage values corresponding to respective radiation field sizes at the plane of the receptor, and conductive tap means in electrical contact with the signal divider means and coupled to the shutter aperture for selecting from the series a voltage value corresponding to the actual associated field size at the plane of the receptor.

3. A radiographic system as set forth in claim 1 wherein the source-to-image distance sensing means includes a source-to-image distance potentiometer comprising an elongated resistive element having an incremental portion thereof electrically contacted by a wiper arm and having established along its length a graduated series of voltage values corresponding to respective source-to-image receptor distances, and the shutter aperture size sensing means comprises a shutter aperture potentiometer having a resistive element electrically connected to the wiper arm of the source-to-image distance potentiometer and a wiper arm coupled to the adjustable shutter aperture.

4. A radiographic system as set forth in claim 1 wherein the automatic means also includes receptor size sensing means for producing an electrical reference signal corresponding to an equivalent defining dimension of the image receptor size.

5. A radiographic system comprising:
means for directing an x-ray beam from a source through an adjustable shutter aperture means and onto an image receptor located at a selected distance from the source; and
automatic means for adjusting the size of the aperture in accordance with the size of the receptor and the source-to-image receptor distance,
said automatic means including source-to-image distance sensing means for producing an output electrical signal corresponding to the source-to-image receptor distance; shutter aperture size sensing means connected to the output of the source-to-image distance sensing means for modifying said signal in accordance with a defining dimension of the actual shutter aperture size and producing an associated field size electrical signal corresponding to the actual radiation field size at the plane of the receptor; and receptor size sensing means for producing an electrical reference signal corresponding to an equivalent defining dimension of the image receptor size.

6. A radiographic system as set forth in claim 5 wherein the automatic means includes collimator monitoring means for comparing the field size signal to the reference signal and providing an output signal corresponding to the direction and amount of shutter aperture adjustment necessary to produce a resultant field size signal substantially equal to the reference signal.

7. A radiographic system as set forth in claim 6 wherein the automatic means includes electromechanical drive means electrically connected to the output of the collimator monitoring means for receiving said output signal therefrom, and operatively coupled to the adjustable shutter aperture means for adjusting the shutter aperture in accordance with said output signal.

8. A radiographic system as set forth in claim 7 wherein the automatic means includes respective detecting means for producing electrical signals indicative of an image receptor installed in place to receive the beam of radiation, and indicative of a source-to-image receptor distance properly selected.

9. A radiographic system as set forth in claim 8 wherein the collimator monitoring means includes detector monitoring circuit means having respective input terminals electrically connected to said respective detecting means.

10. A radiographic system as set forth in claim 9 wherein the detector monitoring circuit means includes gating means for producing an output electrical signal indicative of an installed image receptor and a selected source-to-image receptor distance.

11. A radiographic system as set forth in claim 10 wherein the detector monitoring circuit means includes monostable multivibrating means electrically connected to the gating means for producing output electrical pulse signals indicative of respective changes in image receptor sizes and in source-to-image receptor distances.

12. A radiographic system as set forth in claim 11 wherein the collimator monitoring means includes a safety interlock circuit means electrically connected to the detector monitoring circuit means for switching automatically from a manual mode of operation to an automatic mode or vice versa depending on the installation or removal, respectively, of an image receptor.

13. A radiographic system as set forth in claim 12 wherein the safety interlock circuit means includes means for preventing generation of the beam of radiation pending the adjustment of the shutter aperture means to obtain a field size signal substantially equal to the reference signal.

14. A radiographic system as set forth in claim 11 wherein the collimator monitoring means also comprises sensor monitoring circuit means for receiving the actual field size electrical signal from the shutter aperture size sensing means, and the electrical reference signal from the receptor size sensing means, in addition to the output signal from the gating means and the output signal from the monostable multivibrating means in the detector monitoring circuit, sensing any substantial difference in voltage between the actual field size electrical signal and the electrical reference signal, and producing an electrical drive signal for operating the electro-mechanical drive means.

15. A radiographic system as set forth in claim 14 wherein the sensor monitoring circuit means includes an electrical comparator having respective input terminals connected to the shutter aperture size sensing means and the receptor size sensing means and means for producing an electrical signal indicative of the difference between the radiation field size and the image receptor size.

16. A radiographic system as set forth in claim 15 wherein the sensor monitoring circuit means includes a flip-flop device having respective terminals connected to the output of the comparator, the output of said gating means, the output of said monostable multivibrating means and having means for latching the flip-flop in a particular mode of operation.

17. A radiographic system as set forth in claim 16 wherein the sensor monitoring circuit means includes a transient protection gating means for producing an electrical signal indicative of the output of the flip-flop device and the gating means in the detector monitoring circuit.

* * * * *